(12) United States Patent
Endo

(10) Patent No.: US 11,347,047 B2
(45) Date of Patent: May 31, 2022

(54) OBSERVATION UNIT AND ENDOSCOPE

(71) Applicant: OLYMPUS CORPORATION, Tokyo (JP)

(72) Inventor: Yasuomi Endo, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/220,512

(22) Filed: Apr. 1, 2021

(65) Prior Publication Data

US 2021/0247604 A1 Aug. 12, 2021

Related U.S. Application Data

(63) Continuation of application No. PCT/JP2018/037191, filed on Oct. 4, 2018.

(51) Int. Cl.

| *A61B 1/012* | (2006.01) |
| *G02B 23/24* | (2006.01) |
| *A61B 1/05* | (2006.01) |
| *A61B 1/06* | (2006.01) |
| *H04N 5/225* | (2006.01) |

(52) U.S. Cl.
CPC .......... *G02B 23/2484* (2013.01); *A61B 1/012* (2013.01); *A61B 1/051* (2013.01); *A61B 1/0684* (2013.01); *G02B 23/2461* (2013.01); *H04N 5/2253* (2013.01); *G02B 23/243* (2013.01); *H04N 2005/2255* (2013.01)

(58) Field of Classification Search
CPC ....... A61B 1/012; A61B 1/051; A61B 1/0684; G02B 23/2484; G02B 23/2461; H04N 5/2253
USPC .......................................................... 348/68
See application file for complete search history.

(56) References Cited

U.S. PATENT DOCUMENTS

2010/0016672 A1 1/2010 Segawa et al.
2014/0213850 A1 7/2014 Levy et al.

FOREIGN PATENT DOCUMENTS

| EP | 2140798 A1 | 1/2010 |
| JP | 3780072 B2 | 5/2006 |
| JP | 2008-272439 A | 11/2008 |
| JP | 2010-091986 A | 4/2010 |
| JP | 2011-019570 A | 2/2011 |
| JP | 2014-524303 A | 9/2014 |

(Continued)

OTHER PUBLICATIONS

International Search Report dated Dec. 25, 2018 issued in PCT/JP2018/037191.

*Primary Examiner* — Nguyen T Truong
(74) *Attorney, Agent, or Firm* — Scully, Scott, Murphy & Presser, P.C.

(57) ABSTRACT

An observation unit includes a printed circuit board, an image pickup device including an image pickup surface, at least one light-emitting diode, an optical frame to which optical members are fixed, and a convex portion. The printed circuit board includes a rectangular substrate on which the image pickup device is mounted, at least one strip-shaped substrate extending from a side corresponding to the one side of the rectangular substrate, the at least one strip-shaped substrate including, on an end face side, a light-emitting device arrangement portion on which the light-emitting diode is mounted, and a wiring substrate provided with a terminal on an end face side where the wiring substrate extends by a predetermined length from another side crossing the side of the rectangular substrate.

6 Claims, 17 Drawing Sheets

(56) References Cited

FOREIGN PATENT DOCUMENTS

| | | |
|---|---|---|
| JP | 2016-540571 A | 12/2016 |
| JP | 2018-033503 A | 3/2018 |
| WO | 2008/123465 A1 | 10/2008 |
| WO | 2015/084442 A1 | 6/2015 |

OBSERVATION UNIT AND ENDOSCOPE

CROSS REFERENCE TO RELATED APPLICATION

This application is a continuation application of PCT/JP2018/037191 filed on Oct. 4, 2018, the entire contents of which are incorporated herein by this reference.

BACKGROUND OF THE INVENTION

1. Field of the Invention

The present invention relates to an observation unit into which an image pickup device and a light-emitting device are integrated, and an endoscope provided with the observation unit.

2. Description of the Related Art

In medical and industrial fields, endoscopes each equipped with an image pickup optical system and an illumination optical system at a distal end portion of an elongated insertion portion are proposed.

For example, Japanese Patent No. 3780072 discloses an endoscope with an endoscope insertion portion including a concave portion such as a screw hole at a distal end portion, the endoscope being able to maintain appearance quality and repairability of endoscope components satisfactorily.

As illustrated in FIG. 2 and FIG. 4 in the above-described publication, an objective observation unit is inserted in an objective observation unit mounting hole, and a lens frame of the objective observation unit is fixed to a distal end portion body using an objective observation unit fixing screw. The screw hole for the objective observation unit fixing screw of the distal end portion body is filled with a screw hole adhesive, which is a silicone-based adhesive.

An air/water feeding pipe, an insertion channel pipe and a light guide bundle unit are disposed in a mounting hole of the distal end portion body and fixed to the distal end portion body with solder, adhesive or screws.

SUMMARY OF THE INVENTION

An observation unit according to an aspect of the present invention includes a flexible substrate, an image pickup device including a rectangular image pickup surface and mounted on the flexible substrate, at least one light-emitting diode mounted on the flexible substrate on a side of any one side of the rectangular image pickup surface in parallel with the rectangular image pickup surface, an optical frame to which optical members arranged on a front side of the image pickup surface are fixed and a positioning portion configured to engage with an endoscope distal end portion to define an orientation and an arrangement position of the image pickup surface with respect to the endoscope distal end portion. The flexible substrate includes a rectangular substrate on which the image pickup device is mounted, at least one strip-shaped substrate extending from a side corresponding to the one side of the rectangular substrate, the at least one strip-shaped substrate including, on an end face side, a light-emitting device arrangement portion on which the light-emitting diode is mounted, and a wiring substrate provided with a terminal on an end face side where the wiring substrate extends by a predetermined length from another side crossing the side of the rectangular substrate.

An observation unit according to another aspect of the present invention includes a substrate, an image pickup device including a rectangular image pickup surface and mounted on the substrate, at least one light-emitting diode mounted on the substrate on a side of any one side of the rectangular image pickup surface in parallel with the rectangular image pickup surface, an optical frame including a through hole in which optical members arranged on a front side of the image pickup surface are fixed, and a positioning portion configured to engage with an endoscope distal end portion to define an orientation and an arrangement position of the image pickup surface with respect to the endoscope distal end portion. The substrate is rigid and includes an accommodation concave configured to accommodate the optical frame, and the rigid substrate including the accommodation concave includes an image pickup device arrangement portion on a bottom surface of the accommodation concave for the image pickup device to be mounted on, a light-emitting device arrangement portion on an opening-side end face of the accommodation concave for the light-emitting diode to be mounted on, and a convex as the positioning portion.

An endoscope according to an aspect of the present invention includes the above-described observation unit and an endoscope distal end portion provided with a through hole including a positioning groove in which at least the positioning portion of the observation unit is fitted.

DETAILED DESCRIPTION OF THE PREFERRED EMBODIMENTS

Figure 1:
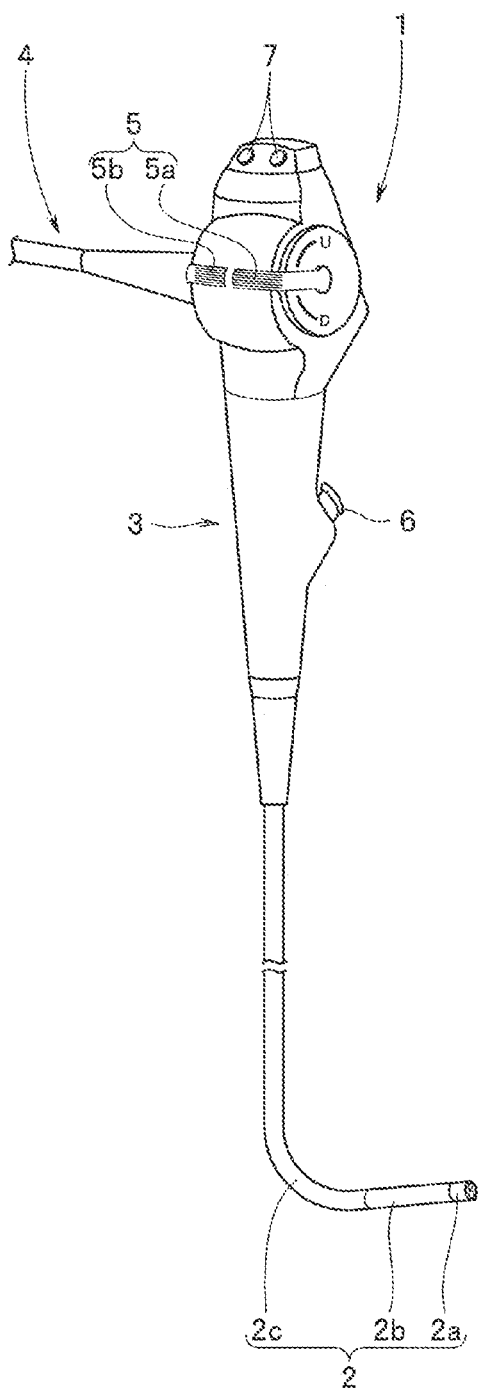
FIG. 1 is a diagram illustrating an endoscope.

Hereinafter, embodiments of the present invention will be described with reference to the accompanying drawings.

Note that in the respective drawings used in the following description, a scale is made to differ for each component so that each component is illustrated in size recognizable in each drawing. In other words, the present invention is not limited to only quantities of components, shapes of the components, a size ratio among the components and relative positional relationships among the components described in the drawings.

As illustrated in FIG. 1, an endoscope 1 includes an insertion portion 2, an operation portion 3 and a universal cord 4. An endoscope distal end portion (hereinafter abbreviated as a "distal end portion") 2a, an endoscope bending portion (hereinafter abbreviated as a "bending portion") 2b and an endoscope flexible tube portion (hereinafter abbreviated as a "flexible tube portion") 2c are disposed at the insertion portion 2 in order from a distal end side.

The bending portion 2b is configured to bend, for example, in up-down, left-right directions. The flexible tube portion 2c is a flexible tube body that can be passively bent.

A distal end side of the operation portion 3 is connected to a proximal end side of the insertion portion 2. The operation portion 3 includes bending operation devices 5, which are operators, a treatment instrument insertion port 6, a plurality of remote switches 7 and a suction port (not shown) or the like. The treatment instrument insertion port 6 communicates with a treatment instrument insertion channel (not shown).

The bending operation devices 5 are operated at a time of bending operation of the bending portion 2b. The bending operation devices 5 are, for example, rotatable levers, including an up-down bending lever 5a and a left-right bending lever 5b.

Figure 2A:
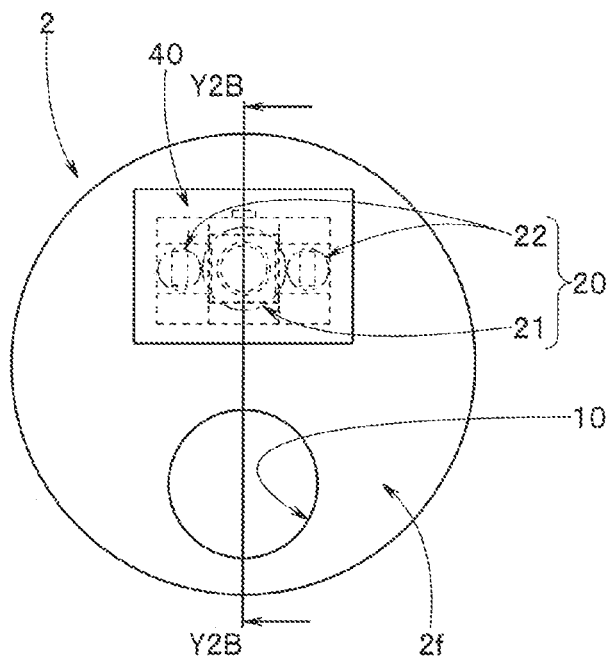
FIG. 2A is a diagram illustrating a distal end face of an insertion portion of the endoscope.
Figure 2B:
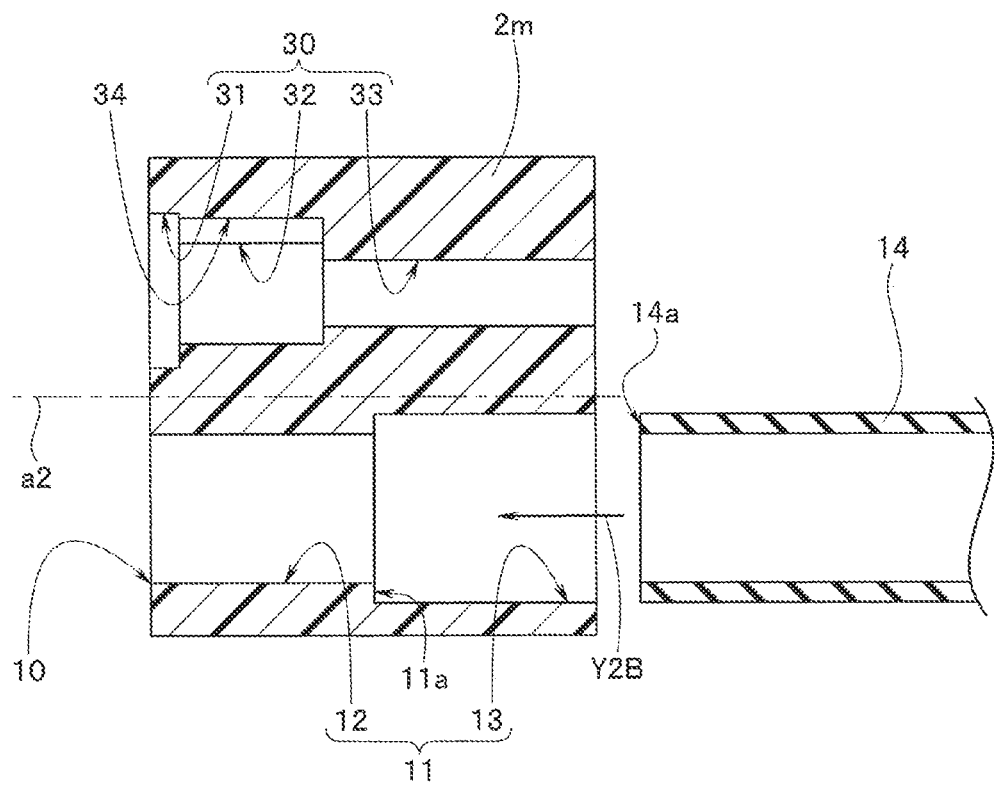
FIG. 2B is a cross-sectional view along an arrow Y2B-Y2B line in FIG. 2A and is a diagram illustrating a distal end component member of the distal end portion.

The distal end portion 2a includes a distal end component member 2m illustrated in FIG. 2A and FIG. 2B. The distal end component member 2m is a rigid member and includes a channel opening 10 and an observation window 20 illustrated in FIG. 2A on a distal end face 2f.

The observation window 20 is rectangular and includes an image pickup window region 21 and illumination window regions 22. Reference numeral 40 denotes an observation unit and the observation window 20 is disposed on a front of the observation unit 40.

As illustrated in FIG. 2B, the distal end component member 2m includes a channel through hole 11 along a longitudinal axis a2 and a unit through hole 30.

The channel opening 10 is a distal end face side opening of the channel through hole 11. The channel through hole 11 is, for example, a stepped hole and includes a small-diameter hole 12 and a large-diameter hole 13. One opening of the small-diameter hole 12 is the channel opening 10.

A distal end portion of a channel tube 14 is supposed to be disposed in the large-diameter hole 13. A distal end portion of the channel tube 14 is fixed in the large-diameter hole 13 by, for example, adhesion.

Reference numeral 11a denotes a stepped surface and is a surface that a distal end face 14a of the channel tube 14 contacts.

The unit through hole 30 is a stepped hole. The unit through hole 30 includes a window hole 31, a unit hole 32 and a wiring hole 33.

The observation unit 40 is supposed to be fixed in the unit hole 32. The observation window 20 is supposed to be fixed in the window hole 31.

Reference numeral 34 denotes a positioning groove. A positioning groove 34 is an engagement portion into which the positioning portion provided in the observation unit 40 (see the convex portion 53 in FIG. 3) fits.

The observation unit 40 will be described with reference to FIG. 3 to FIG. 6B.

Figure 3:
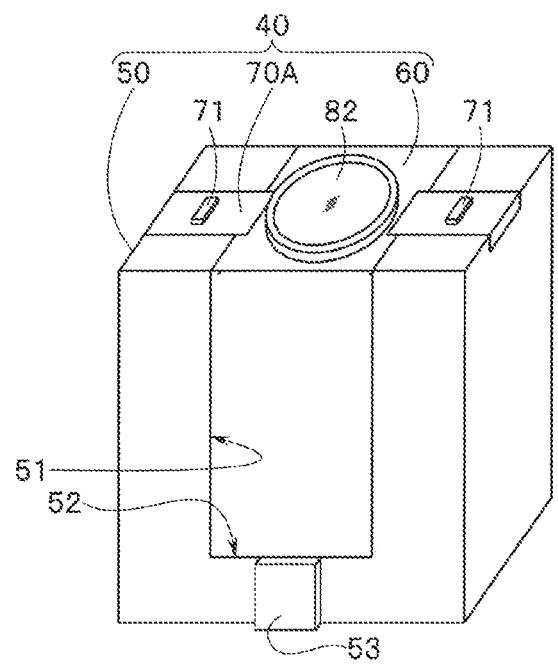
FIG. 3 is a perspective view illustrating an observation unit.

As illustrated in FIG. 3, the observation unit 40 is a substantially rectangular parallelepiped in which a unit body 50, an optical frame 60 and a substrate 70 are integrally disposed.

The optical frame 60 is formed of a rigid member and fixed in an accommodation groove 51 formed in the unit body 50. The accommodation groove 51 is an accommodation concave portion and reference numeral 52 denotes a bottom surface of the accommodation groove 51. Reference numeral 82 denotes a distal end lens and fixed to the optical frame 60.

Figure 4A:
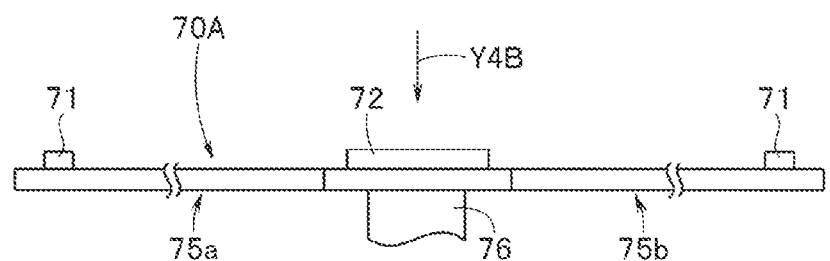
FIG. 4A is a diagram illustrating a flexible printed circuit board.
Figure 4B:
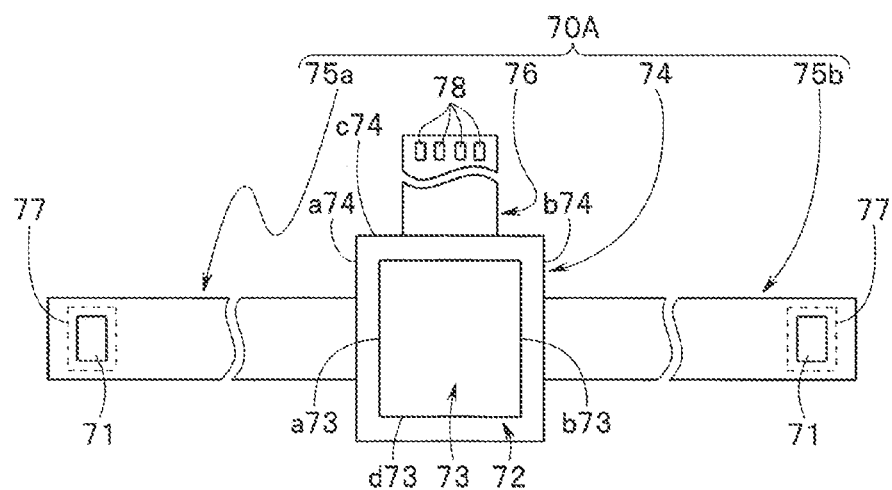
FIG. 4B is a diagram illustrating a flexible printed circuit board viewing from an arrow Y4B direction in FIG. 4A.

In the present embodiment, the substrate 70 is a flexible printed circuit board (hereinafter described as a "printed circuit board 70A"). As illustrated in FIG. 3, FIG. 4A and FIG. 4B, light-emitting diodes 71 and an image pickup device 72 are mounted on the printed circuit board 70A. The light-emitting diodes 71 are illumination optical systems. The image pickup device 72 is an image pickup optical system, and is, for example, a CCD or a C-MOS. The image pickup device 72 includes a rectangular image pickup surface 73.

The printed circuit board 70A includes a rectangular substrate unit 74 and, for example, a pair of strip-shaped substrate units 75a and 75b, and a wiring substrate unit 76.

The rectangular substrate unit 74 is an image pickup device arrangement portion and an image pickup device 72 is mounted on the rectangular substrate unit 74. The image pickup device 72 is fixed so that an orientation of the image pickup surface 73 coincides with a bending direction of the bending portion 2b.

The image pickup device 72 causes a horizontal (scanning) direction of a plurality of pixels (not shown) arrayed on the image pickup surface 73 to coincide with a left-right direction of the bending portion 2b and causes a vertical direction orthogonal to the scanning direction to coincide with the up-down direction of the bending portion 2b.

Of the pair of strip-shaped substrate units 75a and 75b, the first strip-shaped substrate unit 75a extends by a predetermined length from a first vertical substrate unit a74 corresponding to a first vertical image pickup side a73, which is any one side of the image pickup surface 73 and the second strip-shaped substrate unit 75b extends by a predetermined length from a second vertical substrate unit b74 corresponding to a second vertical image pickup side b73 located on an opposite side of the first vertical image pickup side a73 of the image pickup surface 73.

On the other hand, the wiring substrate unit 76 extends by a predetermined length from a horizontal substrate unit c74, which is one side portion crossing the vertical substrate unit a74 or b74 of the image pickup surface 73. A terminal 78 is provided on an end face side of the wiring substrate unit 76. The terminal 78 is an electrical connection portion and a signal line for sending/receiving a signal and a power line for supplying power are connected to the terminal 78.

In the present embodiment, the strip-shaped substrate units 75a and 75b are provided with light-emitting device arrangement portions 77 respectively. The light-emitting device arrangement portions 77 are located on an end face side of the first strip-shaped substrate unit 75a and on an end face side of the second strip-shaped substrate unit 75b respectively.

In other words, the light-emitting diodes 71 in the present embodiment are mounted parallel to the first vertical image pickup side a73, which is any one side of the image pickup surface 73 and are also mounted parallel to the second vertical image pickup side b73 located on an opposite side of the first vertical image pickup side a73.

Figure 5A:
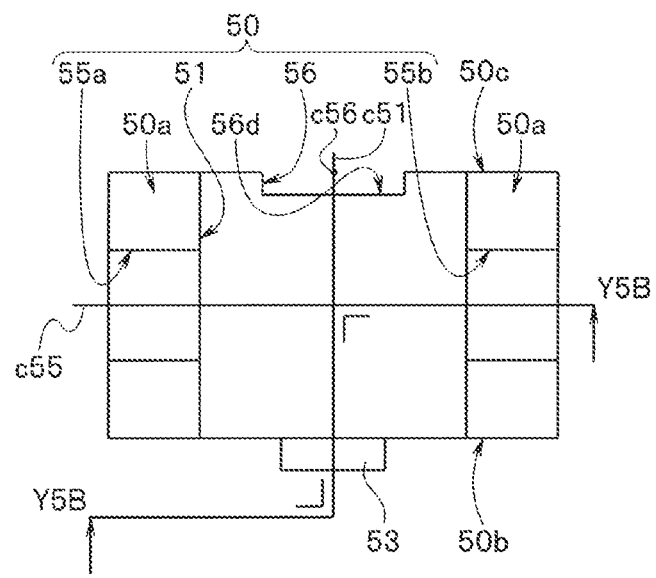
FIG. 5A is a diagram illustrating a unit body.
Figure 5B:
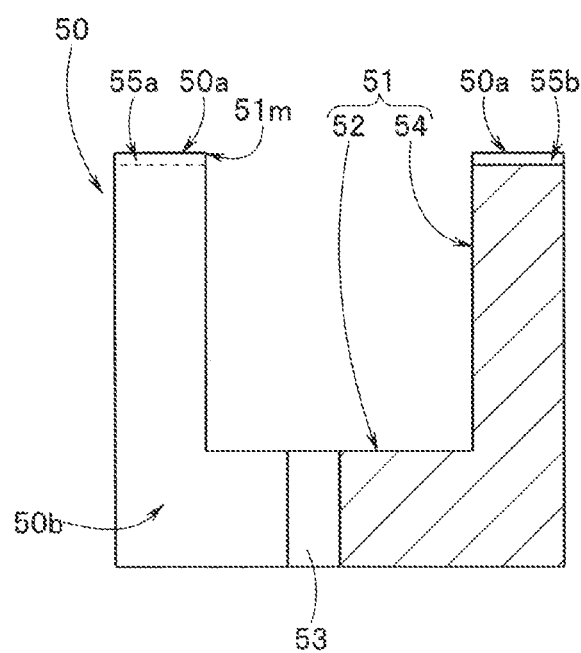
FIG. 5B is a cross-sectional view along an arrow Y5B-Y5B line in FIG. 5A.

As illustrated in FIG. 5A and FIG. 5B, the unit body 50 is formed of a rigid member and includes an accommodation groove 51, a pair of light-emitting device grooves 55a and 55b, a wiring substrate groove 56 and a convex portion 53. The convex portion 53 is a notification portion to indicate an upper direction of the observation unit 40.

Note that the convex portion 53 is not limited to the notification portion to indicate an upper direction of the observation unit 40, but may also be a notification portion to indicate another direction.

The accommodation groove 51, the light-emitting device grooves 55a and 55b and the wiring substrate groove 56 are angular grooves. The accommodation groove 51 is an accommodation portion in which the optical frame 60 is disposed. The accommodation groove 51 includes a bottom surface 52 and facing side wall surfaces 54.

The light-emitting device grooves 55a and 55b are formed on opening-side end faces 50a, which are planes located across an opening 51m of the accommodation groove 51.

A center line c55 of the light-emitting device grooves 55a and 55b is in a positional relationship to be orthogonal to a center line of the accommodation groove 51 (see reference numeral c51 in FIG. 5A).

An end portion side of the strip-shaped substrate unit 75a including the light-emitting device arrangement portion 77 of the first strip-shaped substrate unit 75a mounted with the light-emitting diode 71 is disposed in a first light-emitting device groove 55a.

By contrast, an end portion of the strip-shaped substrate unit 75b including the light-emitting device arrangement portion 77 of the second strip-shaped substrate unit 75b mounted with the light-emitting diode 71 is disposed in a second light-emitting device groove 55b.

Depths of the light-emitting device grooves 55a and 55b are set to be slightly larger than a thickness of the printed circuit board 70A.

A rectangular substrate unit 74 mounted with the image pickup device 72 is supposed to be disposed on the bottom surface 52. In such an arrangement state, a second horizontal image pickup side d73 of the image pickup surface 73 is disposed close to the convex portion 53.

In such an arrangement state, parts other than the end portion side of the first strip-shaped substrate unit 75a and parts other than the end portion side of the second strip-shaped substrate unit 75b are disposed along the side wall surface 54.

The wiring substrate groove 56 is provided on the other end face 50c opposite to one end face 50b from which the convex portion 53 protrudes. The center line c56 of the wiring substrate groove 56 is orthogonal to the center line c51 of the accommodation groove 51.

In addition to the wiring substrate unit 76, a protrusion portion of the optical frame 60 (reference numeral 63 in FIG. 6B) is disposed in the wiring substrate groove 56. Therefore, the depth of the wiring substrate groove 56 is set in advance to be larger than a combined thickness of the wiring substrate unit 76 and the protrusion portion 63.

Figure 6A:
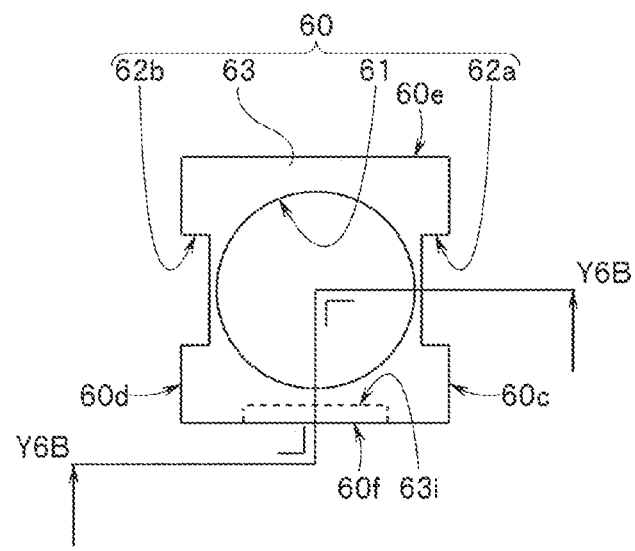
FIG. 6A is a diagram illustrating a lens frame.
Figure 6B:
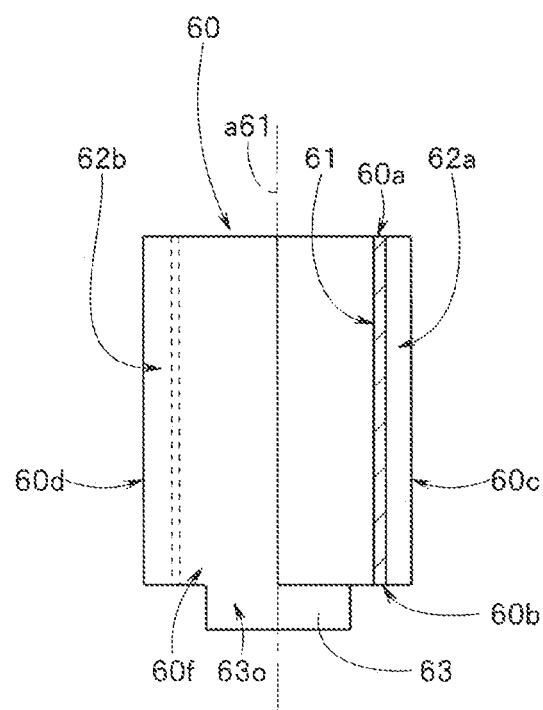
FIG. 6B is a cross-sectional view along an arrow Y6B-Y6B line in FIG. 6A.

As illustrated in FIG. 6A and FIG. 6B, the optical frame 60 has a rectangular parallelepiped shape and includes an optical member through hole 61, a pair of strip-shaped substrate grooves 62a and 62b, and a protrusion portion 63.

Reference numeral 60a denotes a unit constituting surface, forming one surface of the observation unit 40 in a substantially rectangular parallelepiped shape. Reference numeral 60b denotes an installation surface. The installation surface 60b is supposed to be installed on the rectangular substrate unit 74 to be disposed on the bottom surface 52.

Note that a plurality of surfaces sandwiched between the unit constituting surface 60a and the installation surface 60b are frame side surfaces 60c, 60d, 60e and 60f, and are flat surfaces. The frame side surfaces 60c and 60d are disposed so as to face the side wall surface 54, and the third frame side surface 60e and the fourth frame side surface 60f constitute part of the unit side surface of the observation unit 40.

The pair of strip-shaped substrate grooves 62a and 62b are angular grooves and provided so as to sandwich the optical member through hole 61. The first strip-shaped substrate groove 62a is formed on the first frame side surface 60c. The second strip-shaped substrate groove 62b is formed on the second frame side surface 60d. The strip-shaped substrate grooves 62a and 62b are formed along a central axis a61 of the optical member through hole 61.

A first strip-shaped substrate unit 75a along the one side wall surface 54 is disposed in the first strip-shaped substrate groove 62a and a second strip-shaped substrate unit 75b along the other side wall surface 54 is supposed to be disposed in the second strip-shaped substrate groove 62b. Depths of the strip-shaped substrate grooves 62a and 62b are set in advance to be larger than thicknesses of the strip-shaped substrate units 75a and 75b.

The protrusion portion 63 protrudes by a predetermined length from the installation surface 60b. An external surface 63o of the protrusion portion 63 is coplanar with the fourth frame side surface 60f. A width of the protrusion portion 63 is set so that the protrusion portion 63 is disposed in the wiring substrate groove 56. The protrusion portion 63 and the wiring substrate groove 56 are positioning portions and also serve as a notification portion that notifies the operator of the orientation of the image pickup surface 73.

A thickness of the protrusion portion 63 is set so that a gap is formed between the bottom surface 56d of the wiring substrate groove 56 and an internal surface 63i of the protrusion portion 63 when the protrusion portion 63 is disposed in the wiring substrate groove 56. The wiring substrate unit 76 is supposed to be disposed in the gap.

Figure 6C:
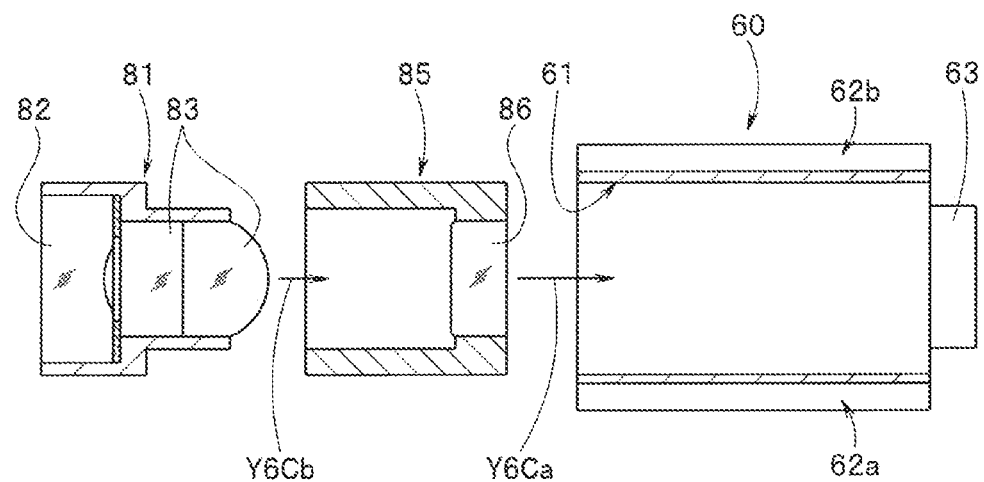
FIG. 6C is a diagram illustrating an objective lens frame and an image pickup frame accommodated in an optical member through hole of the optical frame.

As illustrated in FIG. 6C, an objective lens frame 81 and an image pickup frame 85 having a circular cross section and a pipe shape are supposed to be disposed in the optical member through hole 61 of the optical frame 60 as indicated by arrows Y6Ca and Y6Cb.

A distal end lens 82 and a plurality of optical lenses 83, an aperture (not shown), an interval ring (not shown) or the like are disposed in the objective lens frame 81. On the other hand, a cover glass, a protective glass and the like are disposed in the image pickup frame 85 as an optical member 86.

Figure 6D:
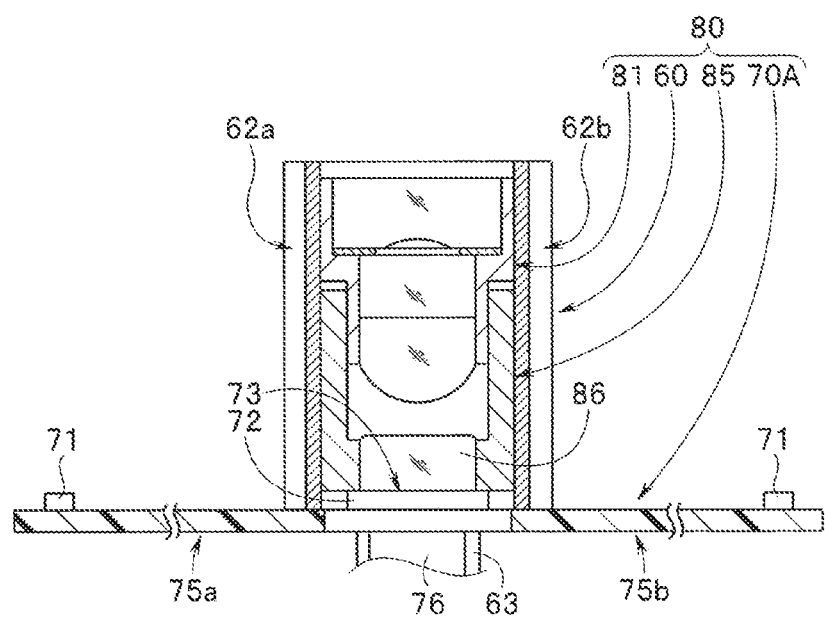
FIG. 6D is a diagram illustrating a unit set.

Reference numeral 80 shown in FIG. 6D denotes the unit set. One surface of the optical member 86 in the unit set 80 is integrally attached in close contact to the image pickup surface 73 of the image pickup device 72 mounted on the rectangular substrate unit 74. The objective lens frame 81 and the image pickup frame 85 are fixed to the optical frame 60 after focus adjustment. The optical frame 60 constitutes an image pickup optical system.

Assembly of the observation unit 40 will be described with reference to FIG. 7A to FIG. 7C.

First, the operator prepares the unit set 80 and the unit body 50.

Figure 7A:
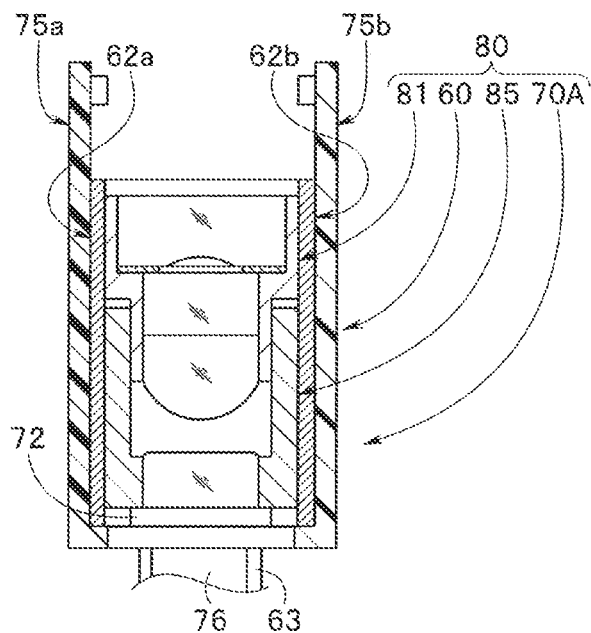
FIG. 7A is a diagram illustrating the unit set with a strip-shaped substrate unit disposed in a strip-shaped substrate groove.

Next, as illustrated in FIG. 7A, the operator disposes the first strip-shaped substrate unit 75a of the unit set 80 outside the first strip-shaped substrate groove 62a and disposes the second strip-shaped substrate unit 75b outside the second strip-shaped substrate groove 62b.

Figure 7B:
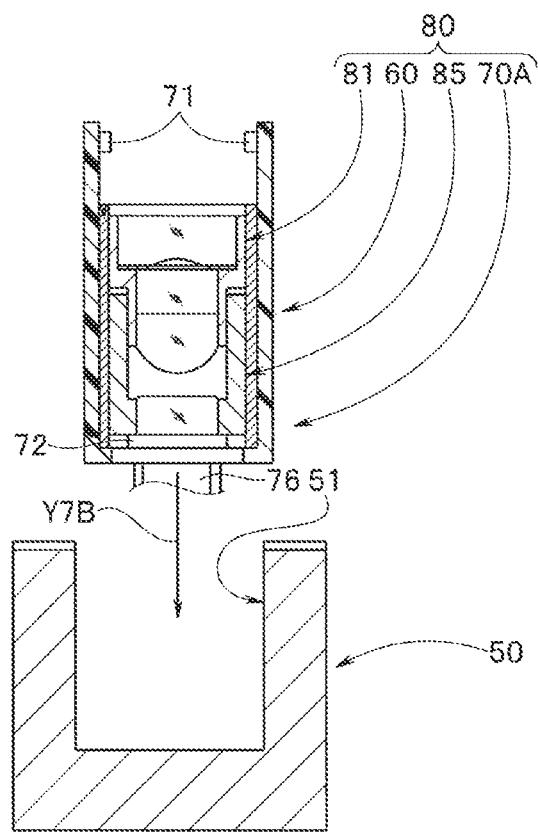
FIG. 7B is a diagram illustrating a step of inserting the unit set in an accommodation groove of the unit body.

Next, as illustrated in FIG. 7B, the operator inserts the aforementioned unit set 80 into the accommodation groove 51 of the unit body 50 as indicated, for example, by an arrow 7B.

At this time, the operator checks positions of the unit set 80 and the unit body 50 so that the wiring substrate unit 76 is disposed in the wiring substrate groove 56.

Figure 7C:
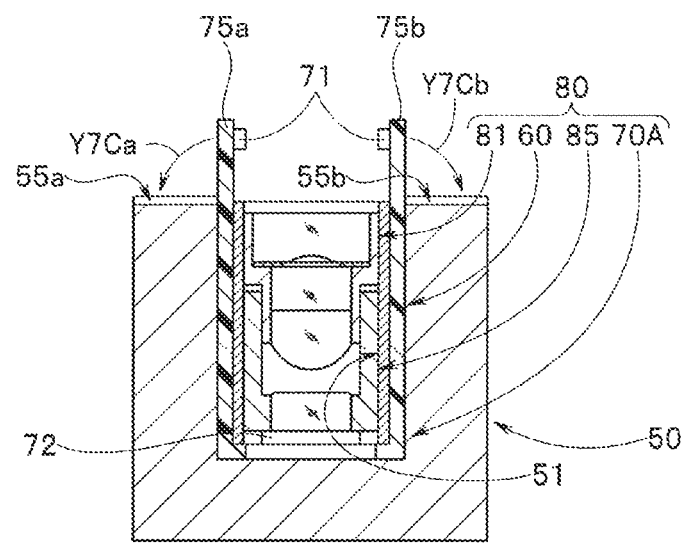
FIG. 7C is a diagram illustrating a step of disposing the unit set in the accommodation groove, and then bending the strip-shaped substrate unit to be disposed in a light-emitting device groove.

As a result, as illustrated in FIG. 7C, the unit set 80 is disposed in the accommodation groove 51.

After this, the operator folds the strip-shaped substrate units 75a and 75b as indicated by arrows Y7Ca and Y7Cb in the drawing so as to be disposed in the light-emitting device grooves 55a and 55b respectively. As a result, the observation unit 40 illustrated in FIG. 3 including the image pickup optical system and the illumination optical system is obtained.

Thus, the observation unit 40 includes the rectangular substrate unit 74 mounted with the image pickup device 72, the printed circuit board 70A including, for example, the pair of strip-shaped substrate units 75a and 75b mounted with the light-emitting diode 71, the accommodation groove 51 to accommodate the optical frame 60 where the objective lens frame 81 and the image pickup frame 85 are disposed and the unit body 50 in which the light-emitting device grooves 55a and 55b are formed to dispose end face sides of the strip-shaped substrate units 75a and 75b on the opening-side end face 50a.

In this way, by disposing the printed circuit board 70A in a predetermined positional relationship for the unit body 50, the image pickup device 72 mounted on the printed circuit board 70A is disposed on the bottom surface 52 and the light-emitting diodes 71 are disposed in the light-emitting device grooves 55a and 55b respectively.

In this way, it is possible to obtain the observation unit 40 including the light-emitting diodes 71 and the image pickup device 72.

The unit set 80 is constructed by fixing the objective lens frame 81 and the image pickup frame 85 in the optical member through hole 61 of the optical frame 60 and disposing the strip-shaped substrate units 75a and 75b in the strip-shaped substrate grooves 62a and 62b respectively formed in the optical frame 60.

The strip-shaped substrate units 75a and 75b are disposed in the strip-shaped substrate grooves 62a and 62b, and the unit set 80 is accommodated in the accommodation groove 51 of the unit body 50 in this way, and it is possible to prevent the strip-shaped substrate units 75a and 75b from getting caught in the side wall surface 54 of the accommodation groove 51 and realize smooth accommodation.

Note that in the aforementioned embodiment, the printed circuit board 70A of the observation unit 40 includes the pair of strip-shaped substrate units 75a and 75b and the strip-shaped substrate units 75a and 75b are provided with the respective light-emitting diodes 71. However, the light-emitting diode 71 may be provided in only one of the first strip-shaped substrate unit 75a and the second strip-shaped substrate unit 75b provided for the printed circuit board 70A.

Figure 8A:
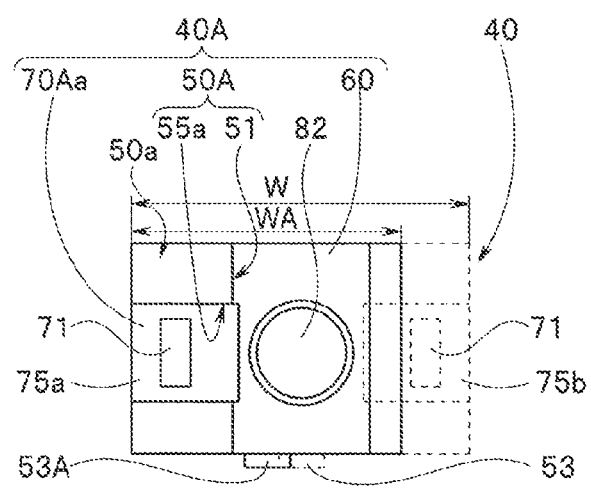
FIG. 8A is a diagram illustrating differences between an image pickup unit with light-emitting diodes provided on both sides across an image pickup surface and an image pickup unit with a light-emitting diode provided only on one side of the image pickup surface.

An observation unit 40A illustrated in FIG. 8A includes a printed circuit board 70Aa, a unit body 50A and the optical frame 60. The printed circuit board 70Aa includes a first strip-shaped substrate unit 75a mounted with the light-emitting diode 71. The unit body 50A includes the accommodation groove 51 to accommodate the optical frame 60 as described above. The optical frame 60 constitutes the aforementioned image pickup optical system.

In the present embodiment, the first light-emitting device groove 55a to dispose the end face side of the first strip-shaped substrate unit 75a is formed on only one opening-side end face 50a of the unit body 50A. Note that the other opening-side end face 50a is a flat surface and is narrower than the one opening-side end face 50a.

Thus, a width WA of the observation unit 40A provided with the one light-emitting diode 71 is smaller than a width W of the observation unit 40. Reference numeral 53A denotes a positioning portion provided for the unit body 50A.

Figure 8B:
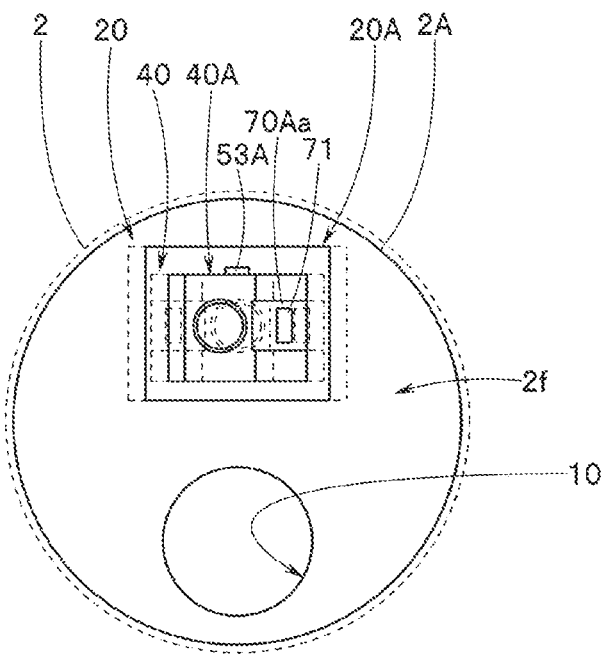
FIG. 8B is a diagram illustrating an image pickup unit provided with a light-emitting diode provided only on one side of the image pickup surface to reduce a diameter of an insertion portion.

As a result, according to the configuration in which an observation window 20A corresponding to the observation unit 40A is disposed on the distal end face 2f, by adjusting arrangement positions of the observation unit 40A and the observation window 20A as illustrated in FIG. 8B, it is possible to make the diameter of the insertion portion 2A smaller than the diameter of the insertion portion 2 and realize the insertion portion of a smaller diameter.

Figure 8C:
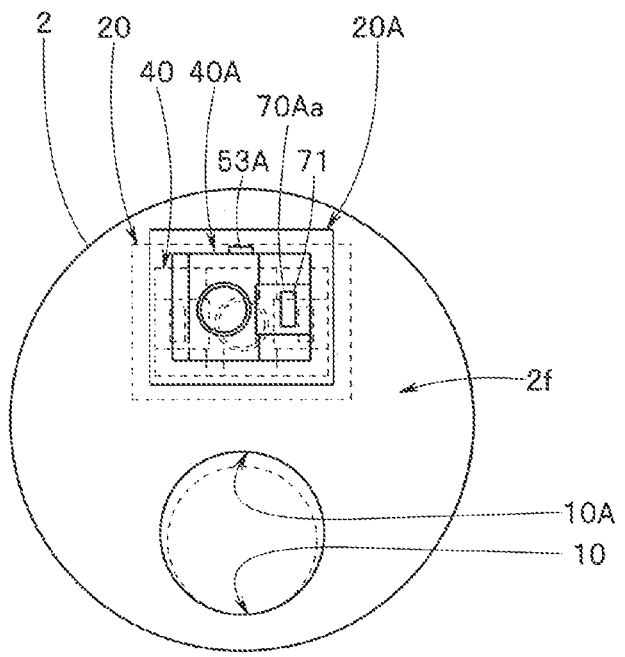
FIG. 8C is a diagram illustrating an image pickup unit provided with a light-emitting diode only on one side of the image pickup surface without changing an outer diameter of the insertion portion to increase a diameter of a channel opening.

On the other hand, by adjusting the arrangement positions of the observation unit 40A and the observation window 20A as illustrated in FIG. 8C, it is possible to realize the channel opening 10A of a larger diameter without changing the outer diameter of the insertion portion 2.

Note that reference numeral 40 denotes the observation unit 40 provided with the two light-emitting diodes 71. A broken line in FIG. 8B shows the insertion portion 2 illustrated in FIG. 2A. A broken line in FIG. 8C shows the channel opening 10 illustrated in FIG. 2A.

In the aforementioned embodiment, the objective lens frame 81 to which the distal end lens 82, the plurality of optical lenses 83, the aperture and the interval ring or the like are fixed and the image pickup frame 85 to which the optical member 86 is fixed, are fixed in the optical member through hole 61 of the optical frame 60. However, the distal end lens 82, the plurality of optical lenses 83, the optical member 86, the aperture and the interval ring or the like may also be directly fixed in the optical member through hole 61 of the optical frame 60.

Assembly of the observation unit 40 into the unit through hole 30 will be described with reference to FIG. 9A and FIG. 9B.

Figure 9A:
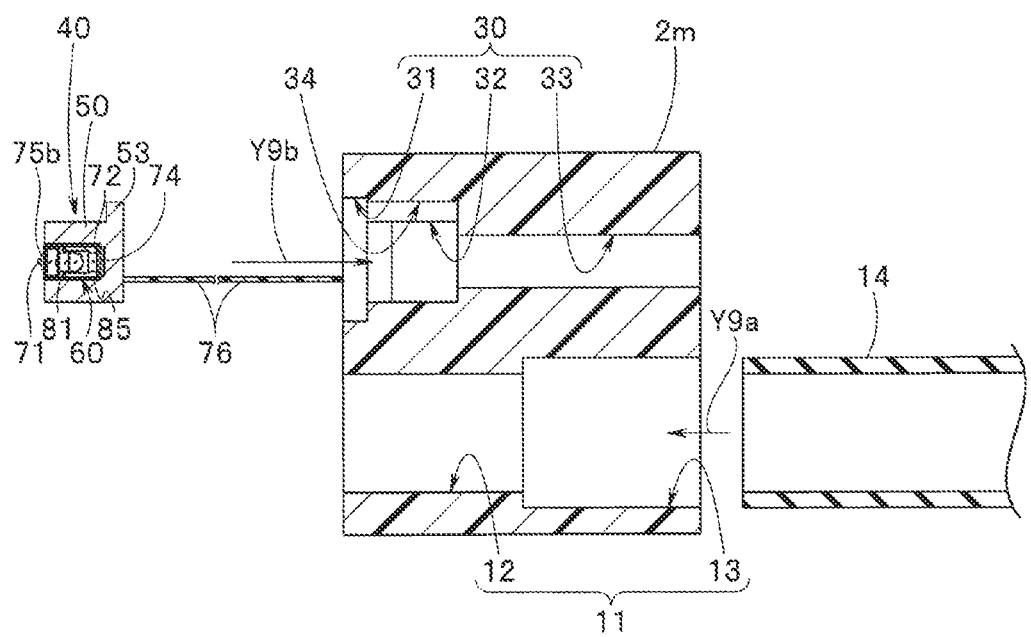
FIG. 9A is a diagram illustrating how a channel tube and an observation unit are attached to a distal end component member.

In the case of the endoscope 1 of the present embodiment, the operator inserts the channel tube 14 into the large-diameter hole 13 of the distal end component member 2m as indicated by an arrow Y9a in FIG. 9A. The channel tube 14 is fixed to the distal end component member 2m as illustrated in FIG. 9B as defined in advance.

On the other hand, the operator aligns the convex portion 53 with the positioning groove 34 and the observation unit 40 is then inserted into the unit through hole 30 of the distal end component member 2m as indicated by an arrow Y9b in FIG. 9A.

In the present embodiment, the observation window 20 is rectangular and the observation unit 40 is substantially rectangular parallelepiped. Therefore, the cross-sectional shape of the window hole 31 and the cross-sectional shape of the unit hole 32 are rectangular.

Note that the observation window 20 is not limited to the rectangular shape, but may be a polygon having four or more sides. The observation unit 40 is not limited to a rectangular parallelepiped shape, that is, a quadrangular prism shape, but may be a polygonal column shape with a polygonal base having four or more sides.

The operator causes the wiring substrate unit 76 of the observation unit 40 to pass through the window hole 31 and the unit hole 32, and guides the wiring substrate unit 76 into the wiring hole 33, and causes the convex portion 53 to pass through the window hole 31 to engage with the positioning groove 34. In this way, the observation unit 40 is positioned in a predetermined positional relationship and disposed in the unit through hole 30.

After that, the operator introduces the observation unit 40 into the unit hole 32, and bonds and fixes the observation unit 40 in this engagement state. As a result, the observation unit 40 is fixed to the distal end component member 2m in a predetermined manner as illustrated in FIG. 9B.

After that, the operator fixes the observation window 20 to the window hole 31 by bonding. This results in the distal end portion 2a configured with the observation unit 40 provided in the distal end component member 2m.

A distal end bending piece of a bending portion set (not shown) constituting the bending portion 2b or one end portion of a tubular bent pipe formed of a superplastic alloy pipe member constituting the bending portion 2b and the flexible tube portion 2c is supposed to be connected to the distal end portion 2a.

In this way, an image pickup optical system in which the image pickup device 72, and, as a plurality of optical members, the distal end lens 82, the optical lens 83, the aperture, the interval ring, and the cover glass or the optical member 86 are arrayed, and an illumination optical system provided with the light-emitting diodes 71 are integrally provided in the observation unit 40.

The distal end component member 2m includes the unit through hole 30 without providing two holes: the observation optical system through hole and the illumination optical system through hole.

Therefore, the observation unit 40 can be inserted from the window hole 31 side, which is an opening on the distal end side of the unit through hole 30 into the unit hole 32 and fixed.

This makes it possible to easily assemble the observation unit 40 into the distal end component member 2m. In addition, it is possible to provide the observation optical system and the illumination optical system at once. As a result, assembly workability can be significantly improved.

Note that in the aforementioned embodiment, the observation unit 40 is fixed to the unit through hole 30 of the distal end component member 2m. However, the observation unit 40 may be disposed in a multi-lumen tube 90. This multi-lumen tube 90 constitutes the insertion portion 2 of the endoscope 1.

The multi-lumen tube 90 includes a channel through hole 91, a unit through hole 92 and a through hole 97 for a plurality of bending wires. Reference numeral 98 denotes a mounting hole.

A distal end hole 93 is formed on a tube distal end face 90f side of the unit through hole 92 of the multi-lumen tube 90. The distal end hole 93 includes a window distal end hole 94, a unit distal end hole 95 and a positioning distal end groove 96.

Figure 10A:
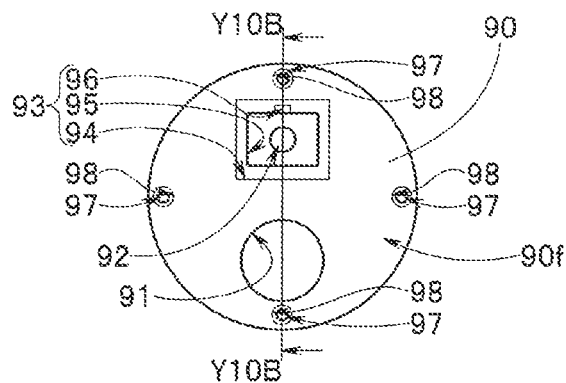
FIG. 10A is a diagram illustrating a distal end face of an insertion portion constituted by a multi-lumen tube.
Figure 10B:
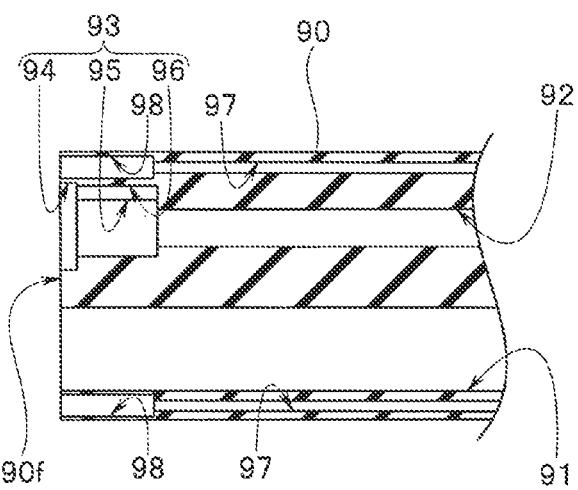
FIG. 10B is a cross-sectional view along an arrow Y10B-Y10B line in FIG. 10A and is a diagram illustrating the distal end portion of the multi-lumen tube.
Figure 10C:
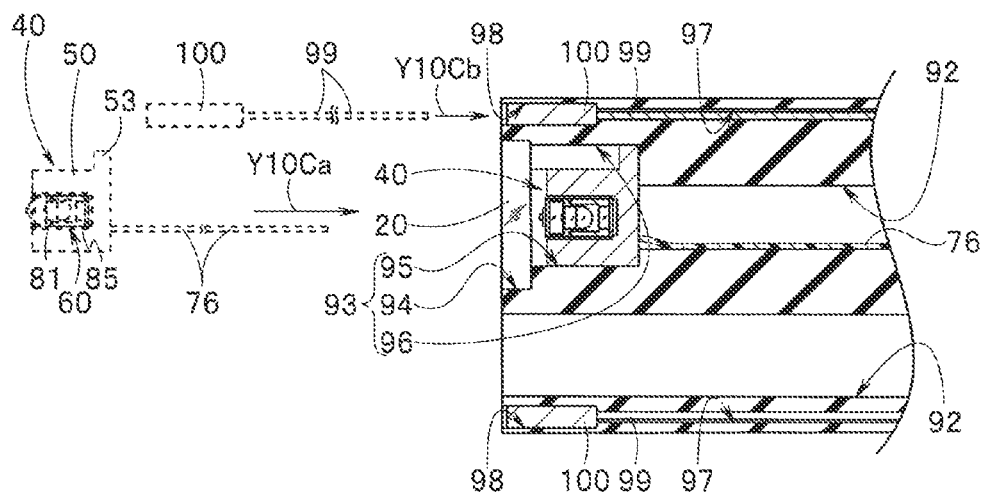
FIG. 10C is a diagram illustrating how the observation unit is attached to a distal end hole of the multi-lumen tube.

According to this configuration, the observation unit 40 is inserted into the distal end hole 93 as indicated by an arrow Y10Ca in FIG. 10C. In this case, the operator causes the convex portion 53 to face the positioning distal end groove 96, causes the wiring substrate unit 76 to pass through the distal end hole 93 and guides the wiring substrate unit 76 to the unit through hole 92.

After that, the operator causes the convex portion 53 to pass through the window distal end hole 94, to engage with the positioning distal end groove 96 and introduces the observation unit 40 into the unit distal end hole 95 while maintaining the engagement state.

As a result, the observation unit 40 is fixed in the distal end hole 93 in a predetermined manner After that, the observation window 20 is fixed in the window distal end hole 94. This results in a configuration of the multi-lumen tube 90 provided with the observation unit 40.

Thus, the distal end hole 93 to fix the observation unit 40 is provided on the distal end face side of the multi-lumen tube 90. As a result, it is possible to eliminate the need for operation of attaching the channel tube and provide the observation optical system and the illumination optical system at once. This makes it possible to further improve the assembly work.

Note that a bending wire 99 passes through a mounting hole 98 provided on a tube distal end face 90f as indicated by an arrow Y10Cb and is guided to the bending wire through hole 97. A wire stopper 100 fixed to an end portion of the bending wire 99 is bonded and fixed in the mounting hole 98 while maintaining watertightness.

An observation unit 40B will be described with reference to FIG. 11A to FIG. 11C.

Figure 11A:
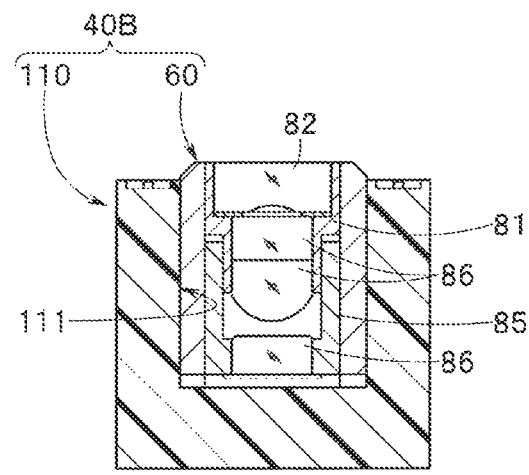
FIG. 11A is a diagram illustrating another configuration of the observation unit.

As illustrated in FIG. 11A, the observation unit 40B is configured by integrally disposing an optical frame 60 and a unit body 110. The unit body 110 also serves as a substrate. The unit body 110 is formed by laminating a plurality of rigid substrates with wiring, electrical connection portions provided at predetermined positions. Note that in FIG. 11A and FIG. 11B, the laminated structure of the unit body 110 is not shown.

Figure 11B:
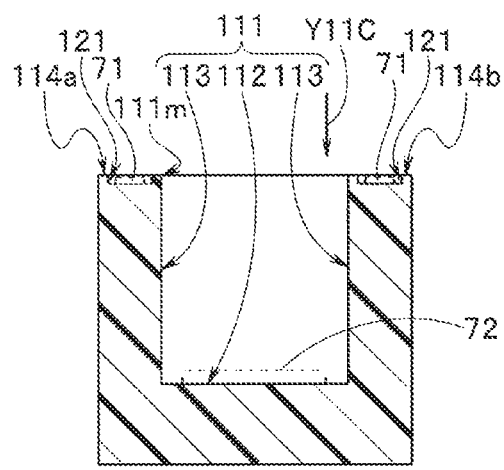
FIG. 11B is a diagram illustrating a unit body also serving as a substrate.
Figure 11C:
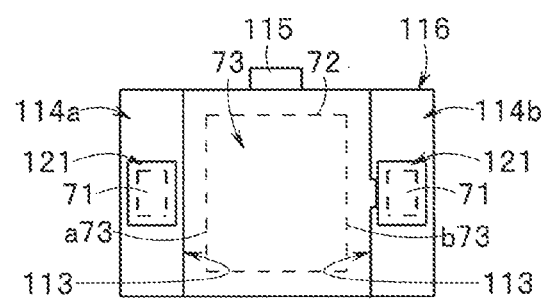
FIG. 11C is a view of the unit body viewing from an arrow Y11C direction in FIG. 11B.

As illustrated in FIG. 11A to FIG. 11C, an accommodation groove 111 is formed in the unit body 110. The accommodation groove 111 is an angular groove similar to the aforementioned accommodation groove, and is an accommodation concave portion configured to accommodate the optical frame 60.

The accommodation groove 111 includes a bottom surface 112 and side wall surfaces 113 facing each other. The bottom surface 112 is an image pickup device arrangement portion and is mounted with the image pickup device 72.

Reference numerals 114a and 114b denote opening-side end faces. The opening-side end faces 114a and 114b are flat surfaces located so as to sandwich an opening 111m of the accommodation groove 111.

As illustrated in FIG. 11C, a light-emitting device arrangement portion 121 is provided at a substantially center of each opening-side end face 114a or 114b. The light-emitting diode 71 is mounted on each light-emitting device arrangement portion 121.

The image pickup device 72 is fixed so that the orientation of the image pickup surface 73 coincides with the bending direction of the bending portion 2b as described above.

Therefore, the light-emitting diode 71 in the present embodiment is mounted in parallel with the first vertical image pickup side a73, which is any one side of the image pickup surface 73, and also mounted in parallel with the second vertical image pickup side b73 located on opposite side of the first vertical image pickup side a73.

Reference numeral 115 denotes a convex portion, which is a notification portion that indicates an upward direction of the observation unit 40B. The convex portion 115 protrudes from one end face 116.

Note that a flexible substrate (not shown), for example, to send/receive a signal and to supply power is connected to the unit body 110 of the observation unit 40B.

Assembly of the observation unit 40B according to the present embodiment will be described.

Figure 12A:
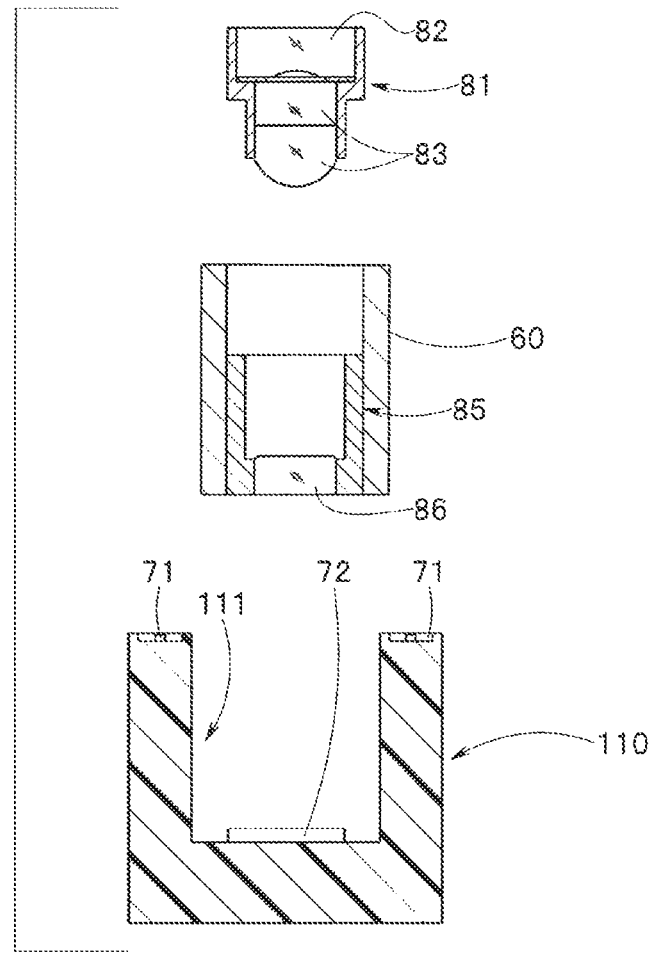
FIG. 12A is a diagram illustrating how the observation unit in FIG. 11A is assembled.

As illustrated in FIG. 12A, the operator prepares the unit body 110 mounted with the light-emitting diodes 71 and the image pickup device 72, the optical frame 60 integral with the image pickup frame 85 to which the optical member 86 is fixed, and the objective lens frame 81 to which a distal end lens 82, the plurality of optical lenses 83, the aperture, the interval ring or the like are fixed.

The operator first inserts the optical frame 60 into the accommodation groove 111 of the unit body 110.

Figure 12B:
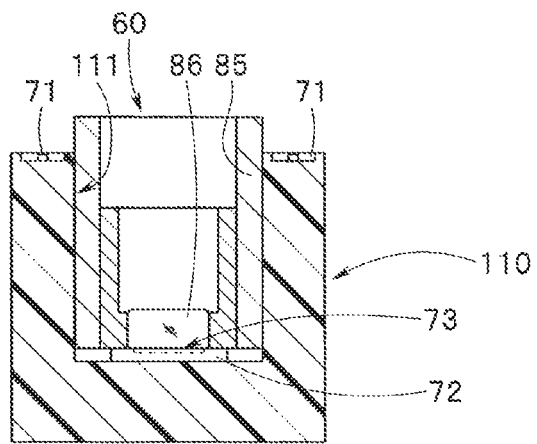
FIG. 12B is a diagram illustrating an optical frame with an integrated image pickup frame fixed in an accommodation groove of the unit body.

As illustrated in FIG. 12B, the operator integrally attaches the optical frame 60 in the accommodation groove 111 while keeping one surface of the optical member 86 in close contact with the image pickup surface 73 of the image pickup device 72.

Figure 12C:
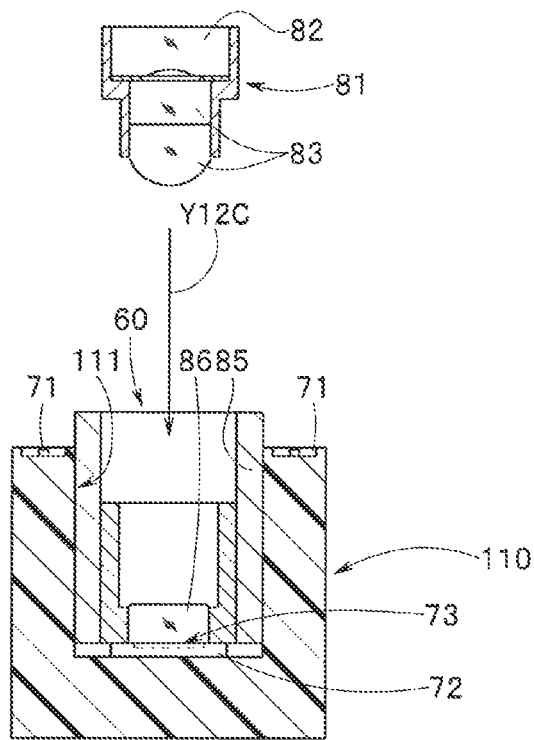
FIG. 12C is a diagram illustrating a step of disposing an objective lens frame with a distal end lens, an optical lens or the like fixed to the optical frame.

After that, as indicated by an arrow Y12C in FIG. 12C, the operator disposes the objective lens frame 81 in the image pickup frame 85. At this time, the objective lens frame 81 is moved within the image pickup frame 85 and fixed to the optical frame 60 while performing focus adjustment.

As a result, the observation unit 40B illustrated in FIG. 11A including the image pickup optical system and the illumination optical system is obtained.

Thus, the observation unit 40B includes the unit body 110 also serving as a substrate and provided with the accommodation groove 111 mounted with the image pickup device 72 and the light-emitting diodes 71, and the optical frame 60 in which the objective lens frame 81 and the image pickup frame 85 are disposed.

Thus, by fixing the optical frame 60 in the accommodation groove 111 of the unit body 110 and performing focus adjustment between the objective lens frame 81 and the image pickup frame 85, it is possible to obtain the observation unit 40B including the light-emitting diodes 71 and the image pickup device 72.

Figure 9B:
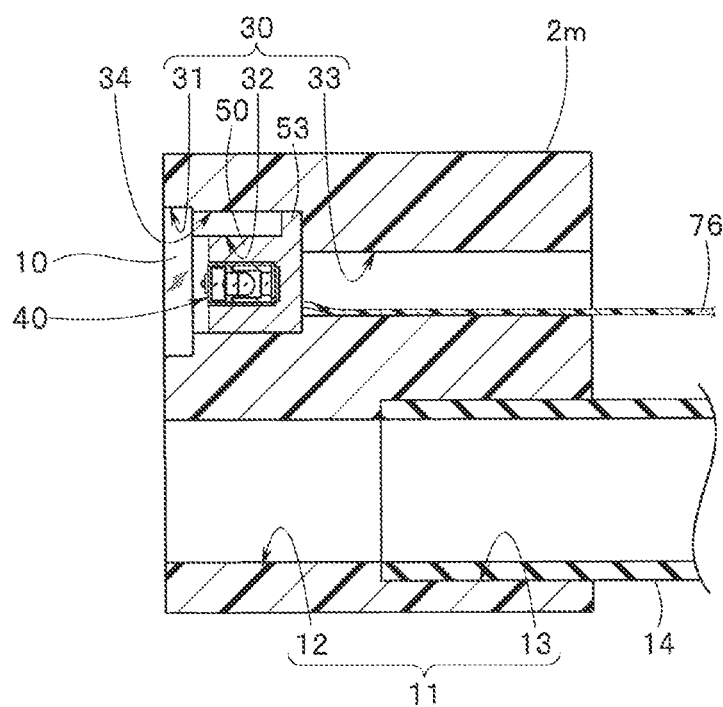
FIG. 9B is a diagram illustrating a distal end component member provided with the channel tube and the observation unit.

The observation unit 40B is assembled into the unit through hole 30 in substantially the same way as with the observation unit 40 illustrated in FIG. 9A and FIG. 9B.

In other words, the operator aligns the convex portion 115 of the observation unit 40B with the positioning groove 34. The operator then inserts the observation unit 40B into the unit through hole 30. After that, the operator causes the convex portion 115 to engage with the positioning groove 34, introduces the observation unit 40B into the unit hole 32 and bonds and fixes the observation unit 40B.

As a result, the observation unit 40B is fixed to the distal end component member 2m in a predetermined manner After that, the operator fixes the observation window 20 to the window hole 31 by bonding. The distal end portion 2a with the observation unit 40B provided at the distal end component member 2m is constituted in this way.

In the same way as with the aforementioned observation unit 40, assembly of the observation unit 40B to the distal end component member 2m can be performed easily. In addition, the observation optical system and the illumination optical system can be provided at once. As a result, assembly workability can be improved significantly.

Note that the observation unit 40B may be fixed to the multi-lumen tube 90 illustrated in FIG. 10A and FIG. 10B.

In the aforementioned endoscopes, the observation units 40, 40A and 40B are inserted from the opening on the distal end side of the unit through hole 30 formed in the distal end component member 2m into the unit hole 32 and fixed. However, the observation unit 40C may also be configured as illustrated in FIG. 13A and FIG. 13B.

Figure 13A:
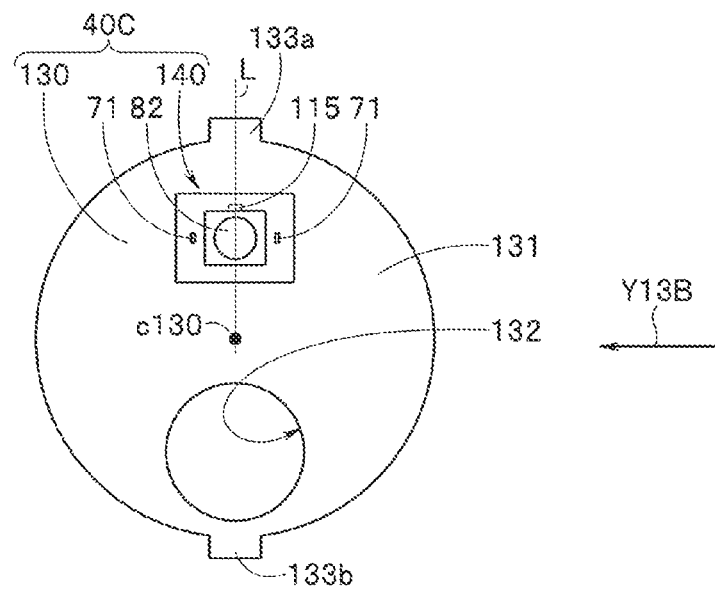
FIG. 13A is a diagram illustrating an observation unit provided with a connection plate and an observation unit.
Figure 13B:
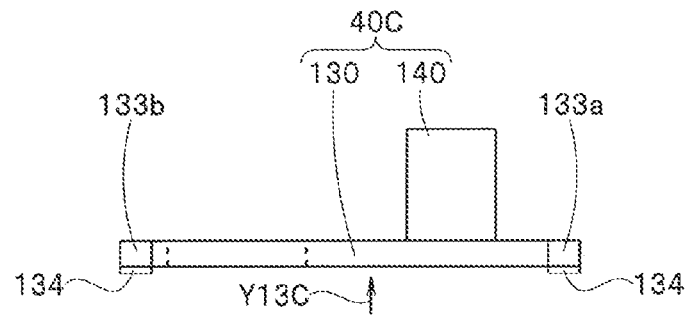
FIG. 13B is a diagram illustrating the observation unit viewing from an arrow Y13B direction in FIG. 13A.

As illustrated in FIG. 13A and FIG. 13B, an observation unit 40C includes a connection plate 130 and an observation unit 140.

The connection plate 130 is a flat disk 131 having a predetermined thickness and includes a channel tube hole 132 and a pair of connection convex portions 133a and 133b at predetermined positions.

The observation unit 140 is substantially the same as the aforementioned observation unit 40B and is integrally fixed to a predetermined position of the connection plate 130.

The observation unit 140 is fixed on the connection plate 130 so that the convex portion 115 and the connection convex portion 133a are located on a straight line L orthogonal to a center c130.

Figure 13C:
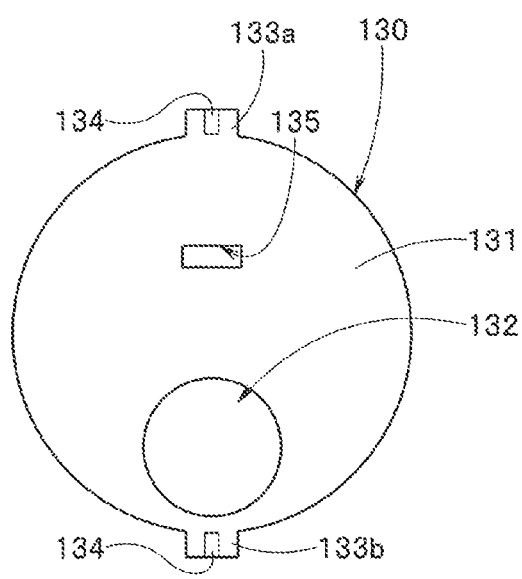
FIG. 13C is a diagram illustrating the observation unit viewing from an arrow Y13C direction in FIG. 13B.

As illustrated in FIG. 13C, connection protrusions 134 are formed at connection convex portions 133a and 133b of the connection plate 130. A cross-sectional shape of the connection protrusion 134 is a curved surface shape, and is, for example, a semicircular shape.

Reference numeral 135 denotes a substrate hole. A flexible substrate 40f connected to the observation unit is configured to pass through the substrate hole 135 and extend to outside.

Figure 13D:
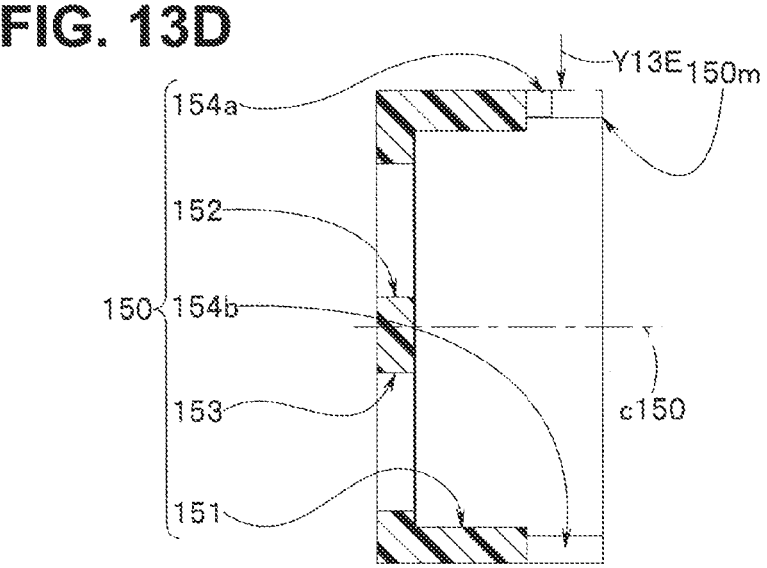
FIG. 13D is a diagram illustrating a distal end frame to which the observation unit is attached.

The aforementioned connection plate 130 is configured to be attached to a cylindrical distal end frame 150 illustrated in FIG. 13D.

The distal end frame 150 includes a frame space 151, a window hole 152, a channel tube mounting hole 153 and a pair of connection grooves 154a and 154b.

Figure 13E:
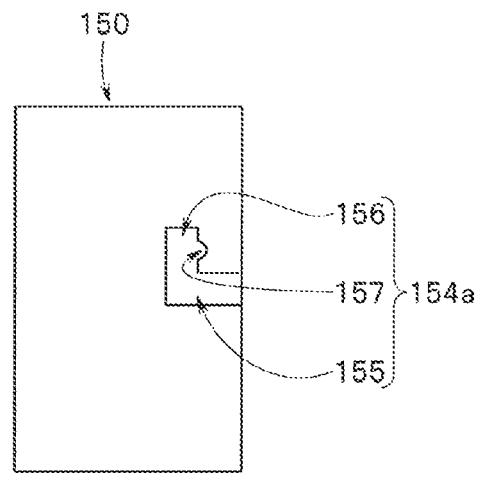
FIG. 13E is a diagram illustrating a distal end frame viewing from an arrow Y13E direction in FIG. 13D.

As illustrated in FIG. 13E, a first connection groove 154a is substantially L-shaped and includes a guide groove 155 and a locking groove 156. The guide groove 155 is formed along a central axis a150 of the distal end frame 150. The locking groove 156 is formed so as to cross the central axis a150.

A connection concave portion 157 is provided on a proximal end side surface of the locking groove 156 on the frame opening 150m side. The connection concave portion 157 includes an axis orthogonal to the central axis a150.

Note that a second connection groove 154b is also formed in the same way as the first connection groove 154a. A distal end bending piece or one end portion of a tubular curved pipe is connected to a frame opening 150m side of the distal end frame 150. The distal end frame 150 is an endoscope distal end portion.

Mounting of the observation unit 40C on the distal end frame 150 will be described with reference to FIG. 13F, FIG. 13G and FIG. 13H.

Figure 13F:
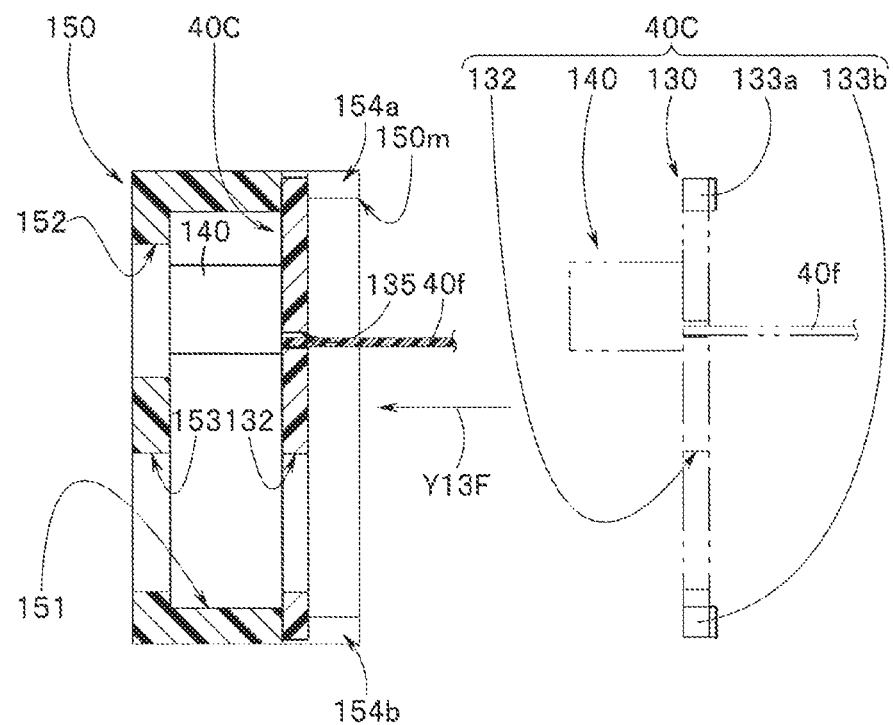
FIG. 13F is a diagram illustrating how the observation unit is attached to the distal end frame.
Figure 13G:
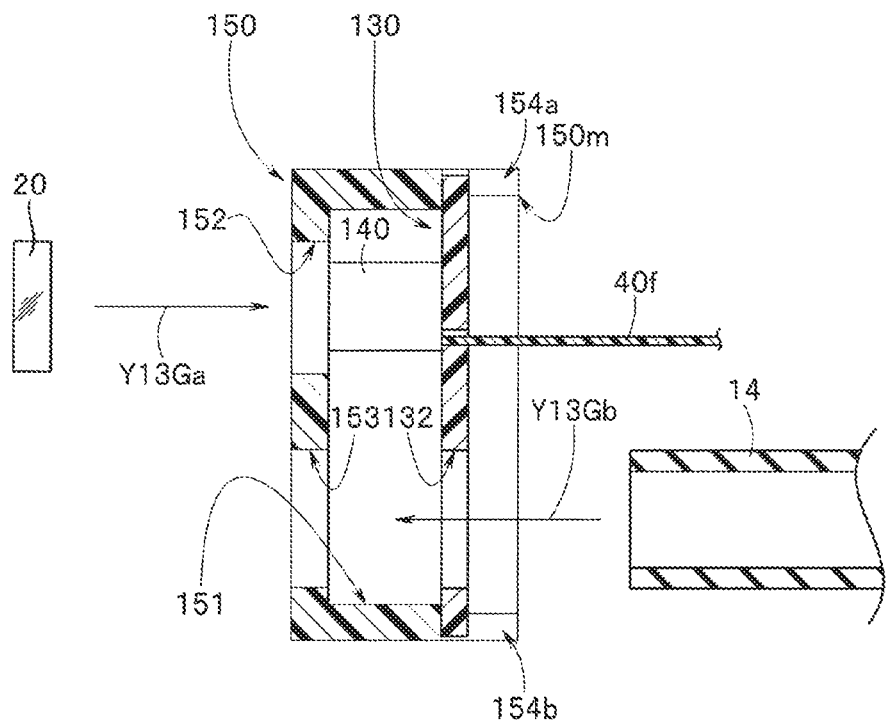
FIG. 13G is a diagram illustrating a step of attaching an observation window and a channel tube to the distal end frame to which the observation unit is attached.
Figure 13H:
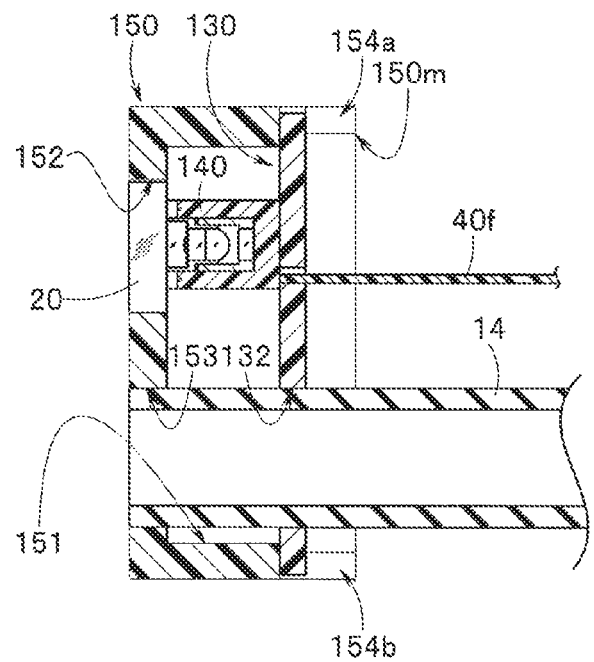
FIG. 13H is a diagram illustrating a distal end frame provided with the channel tube, the observation window and the observation unit.

First, the operator introduces the connection plate 130 as indicated by an arrow Y13F in FIG. 13F from the frame opening 150m side into the frame space 151. Then, as indicated by a solid line, a disk distal end face of the flat disk 131 comes into contact with the distal end side surface facing the proximal end side surface on which the connection concave portion 157 of the locking groove 156 is provided.

Note that when introducing the connection plate 130, the operator causes a first connection convex portion 133a to face the guide groove 155 of the first connection groove 154a and causes a second connection convex portion 133b to face the guide groove 155 of the second connection groove 154b.

Next, the operator rotates the connection plate 130 in a clockwise direction when seen from the frame opening 150m side. Then, the connection convex portions 133a and 133b move in the same direction and go into the locking groove 156. The connection convex portions 133a and 133b further move through the locking groove 156 in the same direction.

As a result, the connection protrusion 134 of the connection convex portion 133a or 133b engages with the connection concave portion 157 of the locking groove 156, and the observation unit 40C is then attached to the distal end frame 150.

After this, as indicated by an arrow Y13Ga, the operator disposes the observation window 20 in the window hole 152, and on the other hand, causes the channel tube 14 to pass through the channel tube hole 132 as indicated by an arrow Y13Gb and disposes the channel tube 14 in the channel tube mounting hole 153.

The observation window 20 is water-tightly fixed to the window hole 152 using an adhesive and the distal end portion of the channel tube 14 is fixed to the channel tube mounting hole 153 using an adhesive.

Thus, the connection convex portions 133a and 133b of the connection plate 130 are disposed in the guide groove 155 and then rotated, the connection convex portions 133a and 133b are introduced into the locking groove 156, and the connection protrusion 134 and the locking groove 156 are caused to engage with each other. This makes it possible to easily attach the observation unit 40C to the distal end frame 150.

Note that a connection protrusion may be formed instead of forming the connection concave portion 157 in the locking groove 156, and a connection concave portion may be formed instead of forming connection protrusions 134 of the connection convex portions 133a and 133b. The gap between the guide groove 155 and the locking groove 156 of the connection grooves 154a and 154b are closed with an adhesive.

What is claimed is:

1. An observation unit comprising:
    a flexible substrate;
    an image pickup device comprising a rectangular image pickup surface and mounted on the flexible substrate;
    at least one light-emitting diode mounted on the flexible substrate on a side of any one side of the rectangular image pickup surface in parallel with the rectangular image pickup surface;
    an optical frame to which optical members arranged on a front side of the image pickup surface are fixed; and
    a positioning portion configured to engage with an endoscope distal end portion to define an orientation and an arrangement position of the image pickup surface with respect to the endoscope distal end portion, wherein the flexible substrate comprises:
    a rectangular substrate on which the image pickup device is mounted;
    at least one strip-shaped substrate extending from a side corresponding to the one side of the rectangular substrate, the at least one strip-shaped substrate comprising, on an end face side, a light-emitting device arrangement portion on which the light-emitting diode is mounted; and
    a wiring substrate provided with a terminal on an end face side where the wiring substrate extends by a predetermined length from another side crossing the side of the rectangular substrate.

2. The observation unit according to claim 1, further comprising a unit body configured to accommodate the flexible substrate and the optical frame, wherein the unit body comprises:
    an accommodation concave comprising a bottom surface on which the rectangular substrate is disposed, the accommodation concave being configured to accommodate the optical frame;
    at least one light-emitting device groove provided on an opening-side end face of the accommodation concave, a portion on the end face side of the strip-shaped substrate being disposed in the at least one light-emitting device groove, the portion comprising the light-emitting device arrangement portion;
a wiring substrate groove in which the wiring substrate and a protrusion of the optical frame are disposed; and
a convex as the positioning portion.

3. The observation unit according to claim 2, wherein a wiring substrate groove having a predetermined depth in which the wiring substrate and the protrusion of the optical frame are disposed is provided on another end face on an opposite side of one end face from which the convex of the unit body protrudes.

4. The observation unit according to claim 2, wherein the optical frame comprises a strip-shaped substrate groove formed on a frame side surface disposed so as to face a side wall surface of the unit body, the strip-shaped substrate being disposed in the strip-shaped substrate groove.

5. An endoscope comprising:
the observation unit according to claim 1; and
an endoscope distal end portion comprising a through hole comprising a positioning groove into which the positioning portion of at least the observation unit is fitted.

6. An observation unit comprising:
a substrate;
an image pickup device comprising a rectangular image pickup surface and mounted on the substrate;
at least one light-emitting diode mounted on the substrate on a side of any one side of the rectangular image pickup surface in parallel with the rectangular image pickup surface;
an optical frame comprising a through hole in which optical members arranged on a front side of the image pickup surface are fixed; and
a positioning portion configured to engage with an endoscope distal end portion to define an orientation and an arrangement position of the image pickup surface with respect to the endoscope distal end portion, wherein
the substrate is rigid and comprises an accommodation concave configured to accommodate the optical frame, and
the rigid substrate comprising the accommodation concave comprises:
an image pickup device arrangement portion on a bottom surface of the accommodation concave for the image pickup device to be mounted on;
a light-emitting device arrangement portion on an opening-side end face of the accommodation concave for the light-emitting diode to be mounted on; and
a convex as the positioning portion.

* * * * *